United States Patent [19]

Gross

[11] Patent Number: 4,687,472
[45] Date of Patent: Aug. 18, 1987

[54] INJECTION ASSISTING APPARATUS

[76] Inventor: Daniel A. Gross, 20218 Wells Dr., Woodland Hills, Calif. 91364

[21] Appl. No.: 929,611

[22] Filed: Nov. 12, 1986

[51] Int. Cl.⁴ ............................................. A61M 5/315
[52] U.S. Cl. ..................................... 604/223; 604/227
[58] Field of Search ............... 604/223, 227, 210, 209, 604/207, 218, 187, 233; 128/765

[56] References Cited

U.S. PATENT DOCUMENTS

| | | |
|---|---|---|
| D. 249,808 | 10/1978 | Bloom et al. |
| 2,678,647 | 5/1954 | Bruger |
| 2,823,674 | 2/1958 | Yochem ............... 604/210 |
| 3,040,744 | 6/1962 | Hoggard ............... 604/210 X |
| 3,118,447 | 1/1964 | Hunt et al. |
| 3,122,280 | 2/1964 | Goda ............... 604/211 X |
| 3,388,941 | 6/1968 | Marcus |
| 3,819,091 | 6/1974 | Hollender ............... 604/223 |
| 4,217,896 | 8/1980 | Behnke |
| 4,324,241 | 4/1982 | Reese |
| 4,351,334 | 9/1982 | Inglefield, Jr. |
| 4,456,017 | 6/1984 | Miles |
| 4,465,478 | 8/1984 | Sabelman et al. |

Primary Examiner—John D. Yasko
Attorney, Agent, or Firm—Kelly, Bauersfeld & Lowry

[57] ABSTRACT

An injection assisting apparatus for use with a disposable syringe includes a primary support attachable to the syringe barrel, a plunger head retainer connected to the primary support by a sliding shaft, and a plurality of finger rings attached to the support and retainer for moving one relative to the other to produce a corresponding movement of the plunger relative to the barrel of the syringe. In one preferred form, the primary support forms a clasp capable of snap-fitting about a portion of the barrel. In another preferred form, the primary support includes an alignment body pivotally connected to a barrel support frame. A thumb ring attached to the retainer is rotated with respect to the plane of the finger rings attached to the primary support, to conform closely to the natural orientation of the thumb with respect to the index and the middle fingers.

23 Claims, 6 Drawing Figures

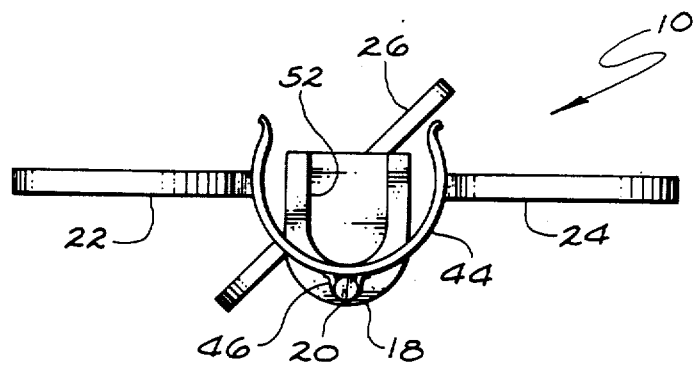
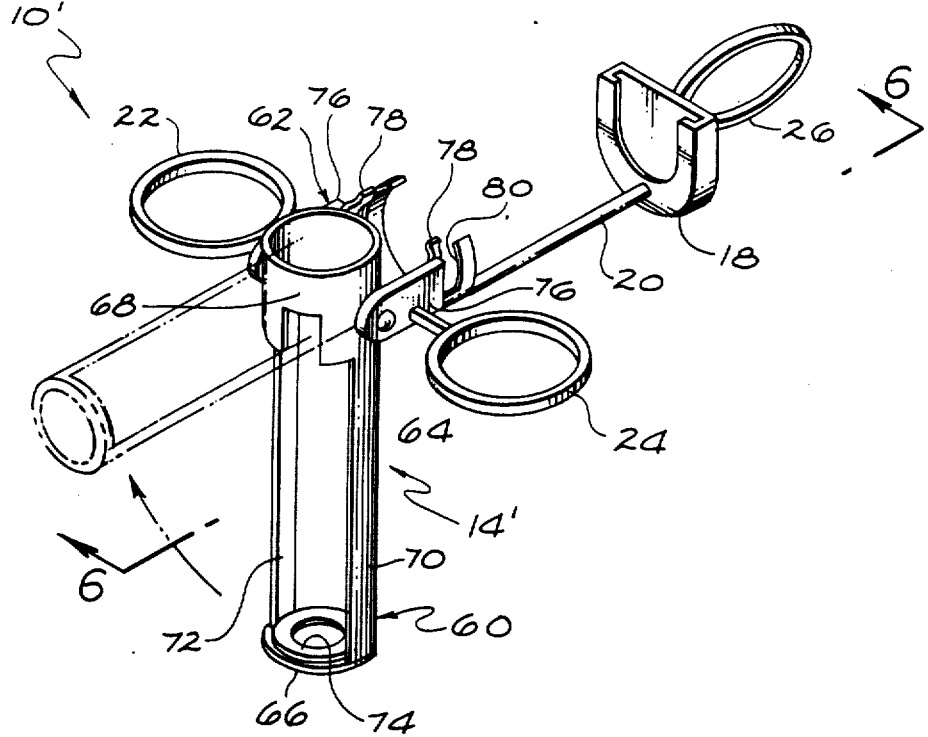
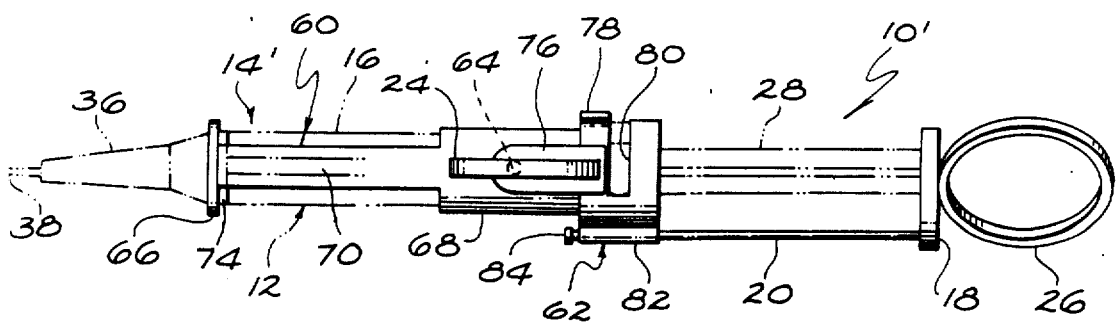

INJECTION ASSISTING APPARATUS

BACKGROUND OF THE INVENTION

This invention relates generally to the subcutaneous, intracutaneous, intramuscular or deeper injection of medications and the like, and, more specifically, to an apparatus for use with disposable syringes, which provides a convenient handling mechanism permitting easy, one-handed, two-way operation of the syringe.

In making subcutaneous injections of certain medications, a grave hazard exists from the possibility that the medication can be unintentionally injected directly into the blood vessel. When a medication and/or biological substance is injected directly into the blood stream, a generalized reaction can occur due to the extent and rapidity of the distribution of the medication and the rapidity of the patient's reaction. In order to eliminate, or at least minimize, this hazard, it is a recommended procedure that after inserting a syringe needle to make an injection, the plunger of the syringe is withdrawn a small amount to create a negative pressure within the injection chamber. If the needle point opening of the syringe has been accidentally placed within the lumen of a blood vessel, the negative pressure within the injection chamber would draw blood immediately into the syringe and, thus, provide an immediate signal to terminate the procedure before the medication is injected. If the negative pressure yields no blood return, then it may be presumed that the needle point opening is positioned outside any blood vessel and the medication may be safely injected into the subcutaneous or intramuscular space where the open end of the needle point has been placed. Because it is an awkward procedure to first withdraw the plunger before injecting the medication, the technician, nurse or physician will frequently omit this initial safety maneuver and will instead directly inject the medication.

It has been known in the art to provide an integral thumb ring on the exposed end of the plunger of a syringe to permit control of the movement of the plunger in both the injecting and retracting or aspirating directions. Such structure would facilitate withdrawl after the needle has been inserted without having to change the grip on the syringe. However, the inclusion of a thumb ring on each syringe adds to the manufacturing cost of a syringe, a factor which is particularly important with respect to disposable syringes. Such disposable syringes can be manufactured in sterile conditions and packaged in sterile containers prior to use, and can even be prefilled with a medicinal fluid at the factory. The provision of a ring integral with the plunger on each syringe would significantly add to the cost of production, as well as adding to the sizes of packages needed to ship and store these syringes.

Previous attempts have been made to provide detachable devices for controlling movement of syringe plungers. Many simply include rings attachable to the plunger head. See, for example, U.S. Pat. Nos. 4,217,896; 4,324,241; and 4,351,334. None, however, has been entirely satisfactory.

Accordingly, there has been a need for a novel injection assisting apparatus which provides a convenient handling mechanism permitting easy, one-handed, two-way operation (aspiration and injection) of a syringe. Additionally, there exists a need for such an apparatus which is capable of accommodating syringes of constant diameter/varying lengths, or syringes of constant length/varying diameters. Further, an injection assisting apparatus is needed which supports the syringe barrel and plunger in a fixed aligned relationship, and which can be constructed economically of material readily sterilized. It would be preferable, moreover, to provide such an injection assisting apparatus with finger and thumb rings oriented to account for the natural angular relationship between the thumb and the index and middle fingers. The present invention fulfills these needs and provides other related advantages.

SUMMARY OF THE INVENTION

The present invention resides in a novel injection assisting apparatus for use primarily with disposable syringes including a barrel having a barrel flange at one end and a barrel shoulder at an opposite end, and a plunger having a first end positioned within the barrel for reciprocation therein and a second end external to the barrel and having a head connected thereto. The injection assisting apparatus comprises, broadly, a primary support attachable to the syringe barrel, a plunger head retainer connected to the primary support by a sliding shaft, and a plurality of finger rings attached to the support and retainer for moving one relative to the other. When properly attached to a syringe, the injection assisting apparatus produces movement of the plunger relative to the barrel of the syringe corresponding to the movement of the retainer with respect to the primary support.

In one preferred form of the invention, the injection assisting apparatus comprises a resilient syringe barrel clasp which is capable of snap-fitting about a portion of the barrel. This barrel clasp includes a clasp body, finger ring means attached to the clasp body, and shaft guide means extending longitudinally along the exterior portion of the clasp body. This clasp body has a horseshoe-shaped cross-section taken perpendicular to its longitudinal axis, and a slot for the positioning of the barrel flange. A shaft slidingly engages the barrel clasp through the shaft guide means, and rigidly supports means for retaining the syringe plunger head in a fixed position relative to an end of the shaft when the syringe barrel is snap-fit into the syringe barrel clasp.

In another preferred form, the injection assisting apparatus comprises a barrel support frame dimensioned to at least partially surround the syringe barrel and provide abutting support for the barrel shoulder, and an alignment body pivotally connected to the barrel support frame. The barrel support frame includes a lower member which circumscribes a portion of the barrel and provides the abutting support for the barrel shoulder, an upper member which circumscribes a portion of the barrel adjacent the barrel flange, and at least one longitudinal member connecting the upper and lower members. Further, a washer is provided which can be removed and replaced by a differently dimensioned washer for adjusting the abutting support provided by the barrel shoulder.

The alignment body includes a support frame clasp and means for retaining the barrel flange in a fixed position when the barrel support frame is snap-fit into the support frame clasp. Further, parallel braces are pivotally connected to the upper member and are oppositely disposed from one another with respect to the barrel support frame.

In a manner similar to that found in the first preferred form, a shaft slidingly engages the alignment body along a line parallel to the longitudinal axis of the barrel support frame when it is snap-fit into the support frame clasp. Moreover, means are provided for retaining the syringe plunger head in a fixed position relative to an end of the shaft as the barrel support frame is rotated with respect to the alignment body to snap-fit the barrel support frame into the support frame clasp.

In both preferred forms, finger rings are rigidly disposed in generally the same plane and on opposite sides of the syringe barrel. A thumb ring is further rigidly attached to the syringe plunger head retaining means, and is rotated with respect to the plane of the finger rings to be oriented in a manner which conforms closely to the natural orientation of the thumb with respect to the index and middle fingers.

Other features and advantages of the present invention will become apparent from the following more detailed description, taken in conjunction with the accompnaying drawings which illustrate, by way of example, the principles of the invention.

BRIEF DESCRIPTION OF THE DRAWINGS

The accompanying drawings illustrate the invention. In such drawings:

FIG. 4 is an end view of the injection assisting apparatus of FIG. 1, taken generally along the line 4—4 of FIG. 2;

FIG. 5 is a perspective view of another preferred form of the injection assisting apparatus of the present invention, shown with a barrel support frame pivoted 90 degrees with respect to an alignment body; and FIG. 6 is an elevational view of the injection assisting apparatus shown in FIG. 5, illustrating, in phantom, the position of a disposable syringe after being placed within the barrel support frame and rotated for alignment with the shaft, and placement of the syringe plunger head within a retainer.

DETAILED DESCRIPTION OF THE PREFERRED EMBODIMENTS

Figure 1:
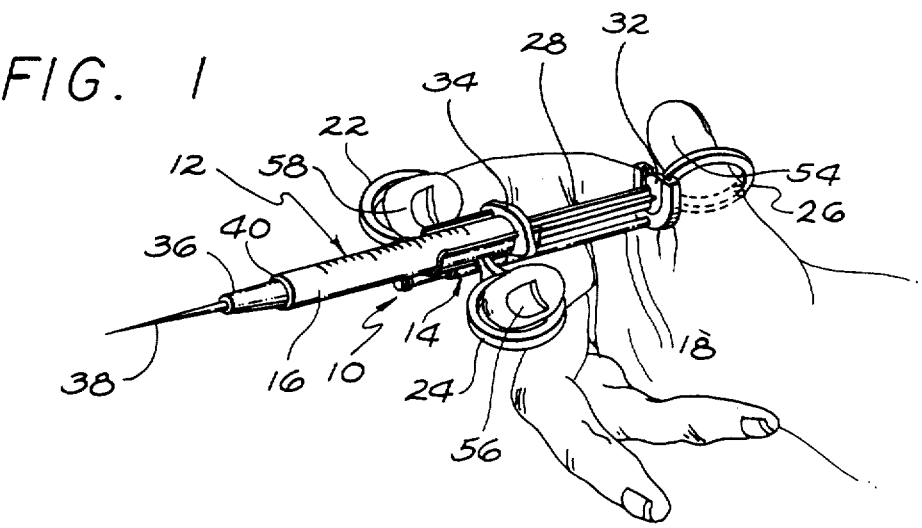
FIG. 1 is a perspective view of one preferred form of an injection assisting apparatus embodying the present invention, shown how it is attached to a disposable syringe and typically used.
Figure 2:
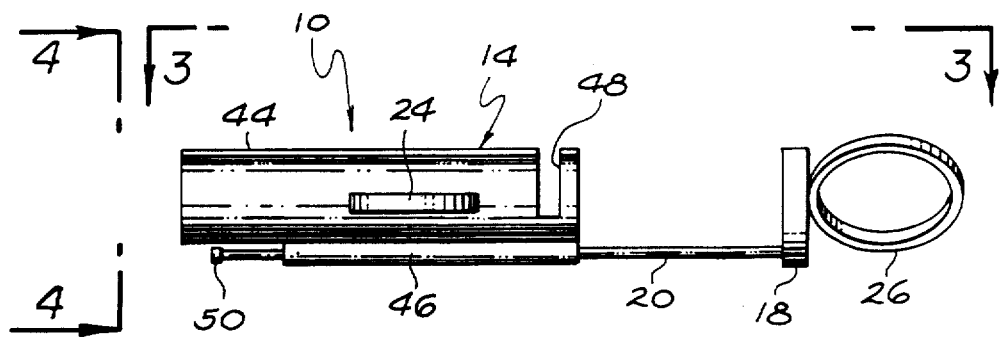
FIG. 2 is an enlarged elevational view of the injection assisting apparatus illustrated in FIG. 1, shown without attachment to the disposable syringe.
Figure 3:
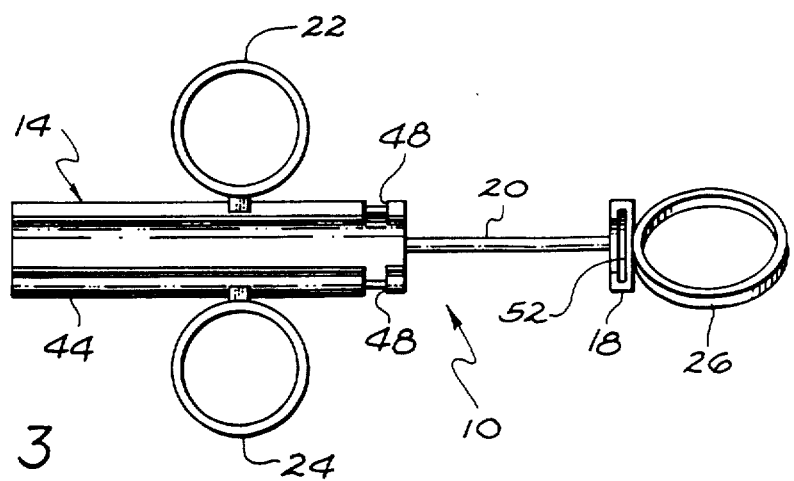
FIG. 3 is a top plan view of the injection assisting apparatus of FIG. 1, taken generally along the line 3—3 of FIG. 2.

As shown in the drawings for purposes of illustration, the present invention is concerned with an injection assisting apparatus, generally designated in FIGS. 1-4 by the reference number 10, and in FIGS. 5 and 6 by the reference number 10'. Each injection assisting apparatus 10 and 10' constructed in accordance with the present invention is intended for use with a disposable syringe 12 and includes, broadly, a primary support structure 14 attachable to a syringe barrel 16, a plunger head retainer 18 connected to the primary support structure by a sliding shaft 20, and a plurality of finger rings 22, 24 and 26 attached to the primary support structure and the plunger head retainer to facilitate movement of one relative to the other.

By way of background information, the disposable syringe 12 comprises the barrel 16 and a plunger 28 having a first end (not shown) positioned in the barrel for reciprocation therein, and a second end external to the barrel and forming a generally circular plunger head (flange) 32. A barrel flange 34 is integrally formed with the barrel 16 and surrounds the opening through which the plunger 28 is inserted. A syringe outlet 36 connected to an injection needle 38 is provided the barrel 16 opposite the barrel flange 34. This outlet 36 further typically includes a stepped portion or barrel shoulder 40.

In accordance with the present invention, and as illustrated with respect to a first embodiment in FIGS. 1-4, the primary support structure 14 comprises a resilient syringe barrel clasp which is capable of snap-fitting about a portion of the barrel 16. More specifically, this barrel clasp includes a clasp body 44 having a horseshoe-shaped cross-section taken perpendicular to its longitudinal axis (FIG. 4), and a shaft guide 46 rigidly affixed to and extending longitudinally along an exterior portion of the clasp body 44. A syringe barrel flange retaining slot 48 is provided near one end of the clasp body 44 for positioning the barrel flange 34 therein. Further, the finger rings 22 and 24 are rigidly affixed to the clasp body 44 and are generally disposed in the same plane but opposite to one another with respect to the clasp body.

Although the syringe barrel clasp 14 can be constructed to accommodate virtually any diameter of syringe barrel 16, it is preferred that the material selected be both strong and somewhat resilient to permit the barrel to be snap-fit into the clasp body 44. Further, in some instances it may be desirable to sterilize the injection assisting apparatus 10 prior to use. In such applications, materials such as stainless steel are preferred.

The shaft 20 is positioned for sliding engagement within the shaft guide 46, and includes an integral shaft travel stop 50 at one end to prevent withdrawal of the shaft from the shaft guide. Opposite this travel stop 50 there is rigidly positioned the plunger head retainer 18. This plunger head retainer 18 is constructed to include a retainer slot 52 positioned and dimensioned to accept the plunger head 32 therein when the syringe barrel 16 is snapped into the clasp body 44.

The thumb ring 26 is attached to the plunger head retainer 18 and is rotated with respect to the plane of the finger rings 22 and 24 to conform to the natural orientation of the thumb 54 with respect to the middle and index fingers 56 and 58. As illustrated best in FIG. 4, the thumb ring 26 is preferably rotated with respect to the plane of the finger rings 22 and 24 approximately 45 degrees. Although not illustrated, it is within the scope of the present invention that the angular orientation of the thumb ring 26 be adjustable to closely conform to the requirements of the user. Moreover, it should be understood that the orientation of the thumb ring 26 depicted in the accompanying drawings will generally meet the needs of a right-handed user. For a left-handed user, the thumb ring 26 would be rotated a like amount in the opposite direction.

To use the injection assisting apparatus 10, all that need be done is simply snap the syringe barrel 16 into the clasp body 44, insuring that the barrel flange 34 is situated within the barrel flange retaining slot 48. The plunger head 32 should also be placed within the retainer slot 52. Such a configuration insures that any movement of the thumb ring 26 relative to the finger rings 22 and 24 will induce corresponding movement of the plunger 28 relative to the barrel 16 of the syringe 12. Further, the construction of the clasp body 44 permits observation of virtually the entire length of the syringe 12. Thus, the injection assisting apparatus 10 of the present invention provides sufficient control over the action of the plunger 28 to permit it to be conveniently and accurately moved in either an injecting or aspirating direction with respect to the barrel 16.

With respect to the second embodiment illustrated in FIGS. 5 and 6, the primary support structure 14 comprises a barrel support frame 60 dimensioned to at least partially surround the syringe barrel 16 and provide abutting support for the barrel shoulder 40, and an alignment body 62 pivotally connected at hinges 64 to the barrel support frame 60. The barrel support frame 60 includes a lower member 66 which circumscribes a portion of the barrel 16 adjacent its outlet 36 and provides the abutting support for the barrel shoulder 40, an upper member 68 which circumscribes a portion of the barrel 16 adjacent the barrel flange 34, and a pair of longitudinal members 70 and 72 which connect the upper and lower members 66 and 68. Additionally, a removable washer is positioned between the longitudinal members 70 and 72 adjacent the lower member 66 to enable the user to configure the injection assisting apparatus 10' to properly use disposable syringes 12 of varying diameters. In particular, this removable washer 74 may be replaced by a differently dimensioned washer for adjusting the direct abutting support provided by the barrel support frame 60 to the barrel shoulder 40.

The alignment body 62 includes a pair of parallel braces 76 pivotally connected by the hinges 64 to the longitudinal members 70 and 72. These parallel braces are attached to a barrel support frame clasp 78 which, in turn, forms a syringe barrel flange retaining slot 80. A shaft guide 82 is affixed to an exterior portion of the support frame clasp 78 and functions in a manner similar to the shaft guide 46 previously described in connection with the first embodiment.

The finger rings 22 and 24 extend outwardly from the parallel braces 76 in a manner very similar to the way in which the finger rings are attached to and extend outwardly from the clasp body 44.

Further, as described in connection with the first embodiment, the shaft 20 is positioned within the shaft guide 82 for sliding engagement with the alignment body 62, and includes a shaft travel stop 84. Although this travel stop 84, as well as the travel stop 50, are illustrated as integrally formed flanges, it will be understood by one skilled in the art that a channel formed in the end of the shaft 20 having a C-ring positioned therein, would form an equivalent structure.

Moreover with respect to the apparatus 10', the plunger head retainer 18 and the thumb ring 26 are positioned, constructed and utilized in an identical manner as that described in connection with the first embodiment.

To utilize the injection assisting apparatus 10', a user should first select an appropriately sized washer 74 having an inner diameter permitting the syringe outlet 36 to pass therethrough while also providing sufficient support for the barrel shoulder 40. While in the configuration illustrated in FIG. 5, the disposable syringe 12 would be inserted into the barrel support frame 60. The barrel support frame 60 would then be pivotted about the hinges 64 until aligned as shown in FIG. 6. As the barrel support frame 60 is pivotted, the barrel flange 34 is placed within the barrel flange retaining slot 80, and the upper member 68 is snap-fit into the support frame clasp 78. Simultaneously, the plunger head 32 is placed within the plunger head retainer 18. When configured as illustrated in FIG. 6, the injection assisting apparatus 10' may be used in a manner identical to that described in connection with the apparatus 10.

From the foregoing it is to be appreciated that the injection assisting apparatus 10 and 10' of the present invention can be constructed in several configurations capable of accommodating syringes of constant diameter/varying lengths, or syringes of constant length/varying diameters. The novel injection assisting apparatus described herein provides a convenient handling mechanism permitting easy, one-handed, two-way operation of the disposable syringe in both the injecting and aspirating directions. Further, the injection assisting apparatus holds the syringe barrel and plunger in a fixed aligned relationship, allows ample visual observation of the syringe 12, and the finger and thumb rings are oriented to account for the natural angular relationship between the thumb and index and middle fingers.

Although two particular embodiments of the invention have been described in detail for purposes of illustration, various modifications of each may be made without departing from the spirit and scope of the invention. Accordingly, the invention is not to be limited, except as by the appended claims.

I claim:

1. An apparatus for making subcutaneous injections, comprising:
    a disposable syringe including a barrel having a barrel flange at one end thereof and a barrel shoulder at an opposite end, and a plunger having a first end positioned in the barrel for reciprocation therein and a second end external to the barrel and having a head connected thereto;
    a pair of finger rings;
    means for positioning the pair of finger rings in a fixed position with respect to the syringe barrel, the finger rings being disposed in generally the same plane and on opposite sides of the disposable syringe;
    a shaft slidingly engaging the finger ring positioning means along a line offset from the syringe but parallel to its longitudinal axis;
    means attached to the shaft for engaging the syringe plunger head; and
    a thumb ring affixed to the plunger head engaging means, wherein the thumb ring is rotated with respect to the plane of the finger rings to be oriented in a plane different from that of the finger rings;
    whereby any movement of the thumb ring relative to the finger rings induces corresponding movement of the plunger relative to the barrel of the syringe.

2. An apparatus as set forth in claim 1, wherein the finger ring positioning means includes a resilient syringe barrel clasp capable of snap-fitting about a portion of the barrel, having a clasp body and shaft guide means extending longitudinally along an exterior portion of the clasp body.

3. An apparatus as set forth in claim 2, wherein the clasp body has a horseshoe-shaped cross section taken perpendicular to its longitudinal axis.

4. An apparatus as set forth in claim 1, wherein the finger ring positioning means includes a barrel support frame dimensioned to at least partially surround the syringe barrel and provide abutting support for the barrel shoulder, and an alignment body pivotally connected to the barrel support frame and including a support frame clasp and means for retaining the barrel flange in a fixed position when the barrel support frame is snap-fit into the support frame clasp.

5. An apparatus as set forth in claim 4, wherein the barrel support frame includes a member which circumscribes a portion of the barrel and provides the abutting support for the barrel shoulder, an upper member which circumscribes a portion of the barrel adjacent the barrel flange, at least one longitudinal member connecting the upper and lower members, and removable washer means which can be removed and replaced by differently dimensioned washer means for adjusting the abutting support provided by the barrel shoulder, and further wherein the alignment body includes parallel braces pivotally connected to the upper member and oppositely disposed from one another with respect to the barrel support frame.

6. An apparatus as set forth in claim 1, wherein the thumb ring is rotated with respect to the plane of the finger rings approximately 45 degrees.

7. An injection assisting apparatus for use with a syringe including a barrel, and a plunger having a first end positioned in the barrel for reciprocation therein and a second end external to the barrel and having a head connected thereto, the injection assisting apparatus comprising:

a resilient syringe barrel clasp capable of snap-fitting about a portion of the barrel and including a clasp body, a pair of finger rings attached to the clasp body and disposed in generally the same plane, and shaft guide means extending longitudinally along an exterior portion of the clasp body;

a shaft slidingly engaging the barrel clasp through the shaft guide means; and means for retaining the syringe plunger head in a fixed position relative to an end of the shaft, the plunger head retaining means including a thumb ring means oriented in a plane different than that of the finger rings;

whereby when the syringe is disposed within the injection assisting apparatus so that the barrel is held securely by the barrel clasp and the plunger head is retained within the retaining means, any movement of the thumb ring means relative to the finger rings will induce corresponding movement of the plunger relative to the barrel of the syringe.

8. An injection assisting apparatus as set forth in claim 7, wherein the clasp body has a horseshoe-shaped cross section taken perpendicular to its longitudinal axis.

9. An injection assisting apparatus was set forth in claim 7, wherein the clasp body includes a slot for the positioning therein of a barrel flange located at one end of the syringe barrel.

10. An injection assisting apparatus as set forth in claim 7, wherein the plunger head retaining means includes a retainer slot for positioning the plunger head therein when the syringe barrel is snap-fit into the barrel clasp.

11. An injection assisting apparatus as set forth in claim 7, wherein the thumb ring means is rotated with respect to the plane of the finger rings to conform to the natural orientation of the thumb with respect to the middle and index fingers.

12. An injection assisting apparatus for use with a syringe including a barrel having a barrel flange at one end and a barrel shoulder at an opposite end, and a plunger having a first end positioned in the barrel for reciprocation therein and a second end external to the barrel and having a head connected thereto, the injection assisting apparatus comprising:

a barrel support frame dimensioned to at least partially surround the syringe barrel and provide abutting support for the barrel shoulder;

an alignment body pivotally connected to the barrel support frame and including a support frame clasp and means for retaining the barrel flange in a fixed position when the barrel support frame is snap-fit into the support frame clasp;

a pair of finger rings rigidly supported by the alignment body;

a shaft slidingly engaging the alignment body along a line parallel to the longitudinal axis of the barrel support frame when it is snap-fit into the support frame clasp; and means for retaining the syringe plunger head in a fixed position relative to an end of the shaft, the plunger head retaining means including a thumb ring;

whereby when the syringe is disposed within the injection assisting apparatus so that the barrel is positioned within the barrel support frame and the barrel support frame is snap-fit into the support frame clasp, and the plunger head is retained within the retaining means, any movement of the thumb ring relative to the finger rings will induce corresponding movement of the plunger relative to the barrel of the syringe.

13. An injection assisting apparatus as set forth in claim 12, wherein the barrel support frame includes a lower member which circumscribes a portion of the barrel and provides the abutting support for the barrel shoulder, an upper member which circumscribes a portion of the barrel adjacent the barrel flange, and at least one longitudinal member connecting the upper and lower members.

14. An injection assisting apparatus as set forth in claim 13, wherein the barrel support frame includes removable washer means which can be removed and replaced by differently dimensioned washer means for adjusting the abutting support provided the barrel shoulder.

15. An injection assisting apparatus as set forth in claim 13, wherein the alignment body includes parallel braces pivotally connected to the upper member and oppositely disposed from one another with respect to the barrel support frame.

16. An injection assisting apparatus as set forth in claim 15, wherein the barrel flange retaining means includes a slot formed, at least in part, by the support frame clasp.

17. An injection assisting apparatus as set forth in claim 12, wherein the retaining means includes a plunger head retainer slot wherein the plunger head can be positioned as the barrel support frame is rotated with respect to the alignment body to snap-fit the barrel support frame into the support frame clasp.

18. An injection assiting apparatus as set forth in claim 12, wherein the finger rings are disposed in generally the same plane and on opposite sides of the alignment body.

19. An injection assisting apparatus as set forth in claim 18, wherein the thumb ring is oriented in a plane different than that of the finger rings.

20. An apparatus for making subcutaneous injections, comprising:

a disposable syringe including a barrel having a barrel flange at one end thereof and a barrel shoulder at an opposite end, and a plunger having a first end positioned in the barrel for reciprocation therein and a second end external to the barrel and having a head connected thereto;

a pair of finger rings;

means for positioning the pair of finger rings in a fixed position with respect to the syringe barrel, the finger ring positioning means including a barrel support frame dimensioned to at least partially surround the syringe barrel and provide abutting support for the barrel shoulder, and an alignment body pivotally connected to the barrel support frame and including a support frame clasp and means for retaining the barrel flange in a fixed position when the barrel support frame is snap-fit into the support frame clasp;

a shaft slidingly engaging the finger ring positioning means along a line offset from the syringe but parallel to its longitudinal axis;

means attached to the shaft for engaging the syringe plunger head; and a thumb ring affixed to the plunger head engaging means;

whereby any movement of the thumb ring relative to the finger rings induces corresponding movement of the plunger relative to the barrel of the syringe.

21. An apparatus as set forth in claim 20, wherein the barrel support frame includes a lower member which circumscribes a portion of the barrel and provides the abutting support for the barrel shoulder, an upper member which circumscribes a portion of the barrel adjacent the barrel flange, and at least one longitudinal member connecting the upper and lower members, and further wherein the alignment body includes parallel braces pivotally connected to the upper member and oppositely disposed from one another with respect to the barrel support frame.

22. An apparatus as set forth in claim 20, wherein the finger rings are disposed in generally the same plane and an opposite sides of the disposable syringe.

23. An apparatus as set forth in claim 22, wherein the thumb ring is rotated with respect to the plane of the finger rings to be oriented in a plane different from that of the finger rings.

* * * * *

UNITED STATES PATENT AND TRADEMARK OFFICE
CERTIFICATE OF CORRECTION

PATENT NO. : 4,687,472

DATED : August 18, 1987

INVENTOR(S) : Daniel A. Gross

It is certified that error appears in the above-identified patent and that said Letters Patent is hereby corrected as shown below:

In Column 1, line 14, delete the word "the" and insert therefor --a--.

In Column 7, line 4, insert --lower--between the words "a" and "member."

In Column 7, line 50, delete the word "was" and insert therefor --as--.

In Column 8, line 60, delete the word "assiting" and insert therefor --assisting--.

Signed and Sealed this

Twenty-eighth Day of June, 1988

Attest:

DONALD J. QUIGG

*Attesting Officer*   *Commissioner of Patents and Trademarks*